(12) United States Patent  
Griffiths

(10) Patent No.: US 7,690,282 B2
(45) Date of Patent: Apr. 6, 2010

(54) SCREW-RETAINING SCREWDRIVER

(75) Inventor: Bryan Griffiths, Coatesville, PA (US)

(73) Assignee: Synthes USA, LLC, West Chester, PA (US)

( * ) Notice: Subject to any disclaimer, the term of this patent is extended or adjusted under 35 U.S.C. 154(b) by 36 days.

(21) Appl. No.: 11/491,407

(22) Filed: Jul. 21, 2006

(65) Prior Publication Data

US 2007/0028728 A1 Feb. 8, 2007

Related U.S. Application Data

(60) Provisional application No. 60/705,668, filed on Aug. 3, 2005.

(51) Int. Cl.
B25B 23/10 (2006.01)
(52) U.S. Cl. ...................................................... 81/460
(58) Field of Classification Search .................. 81/436, 81/460, 461, 451, 441, 443
See application file for complete search history.

(56) References Cited

U.S. PATENT DOCUMENTS

| 2,601,453 | A | * | 6/1952 | Phipard, Jr | 81/460 |
| 2,646,829 | A | * | 7/1953 | Phipard, Jr | 81/460 |
| 2,800,936 | A | * | 7/1957 | West | 81/460 |
| RE24,888 | E | * | 10/1960 | Smith et al. | 81/460 |
| 3,037,539 | A | * | 6/1962 | Johnson et al. | 81/460 |
| 3,234,982 | A | * | 2/1966 | Stillwagon, Jr | 81/460 |
| 3,654,974 | A | * | 4/1972 | Barnes | 81/460 |
| 3,900,057 | A | * | 8/1975 | Benitz | 81/443 |
| 4,779,494 | A | * | 10/1988 | Quach | 81/443 |
| 5,001,948 | A | * | 3/1991 | Weible et al. | 81/436 |
| 5,367,926 | A | * | 11/1994 | Mikic et al. | 81/436 |
| 6,128,983 | A | * | 10/2000 | Arnn | 81/460 |
| 6,176,161 | B1 | * | 1/2001 | Huang et al. | 81/441 |
| D455,943 | S | * | 4/2002 | Lin | D8/86 |
| 6,520,055 | B1 | * | 2/2003 | Reusch et al. | 81/460 |
| 7,077,038 | B2 | * | 7/2006 | Toyooka et al. | 81/460 |
| 7,249,544 | B2 | * | 7/2007 | Totsu | 81/452 |
| 7,452,361 | B2 | | 11/2008 | Kreidler | |

FOREIGN PATENT DOCUMENTS

DE 202004004844 U1 9/2005

* cited by examiner

Primary Examiner—David B Thomas
(74) Attorney, Agent, or Firm—Woodcock Washburn LLP

(57) ABSTRACT

A screwdriver having a retention mechanism for temporarily holding a screw in place on its tip while the screw is being positioned, rotated or removed. More particularly, a screwdriver with a cruciform head used in the installation and removal of bone screws during maxillofacial surgery.

34 Claims, 2 Drawing Sheets

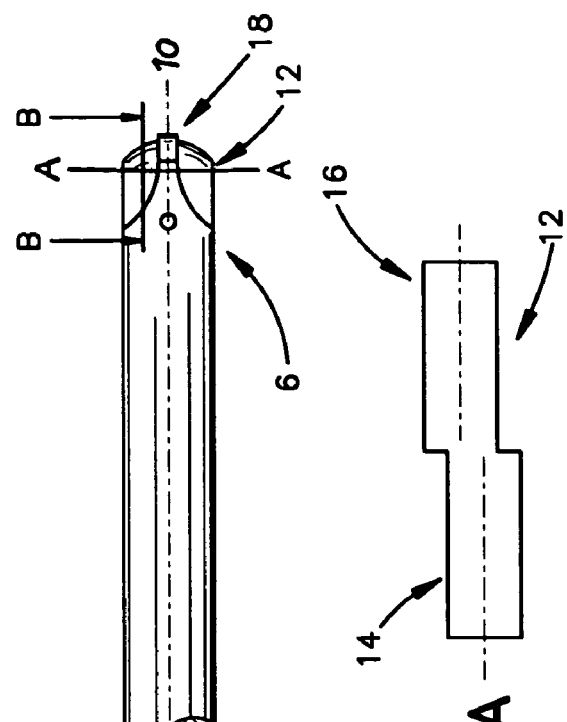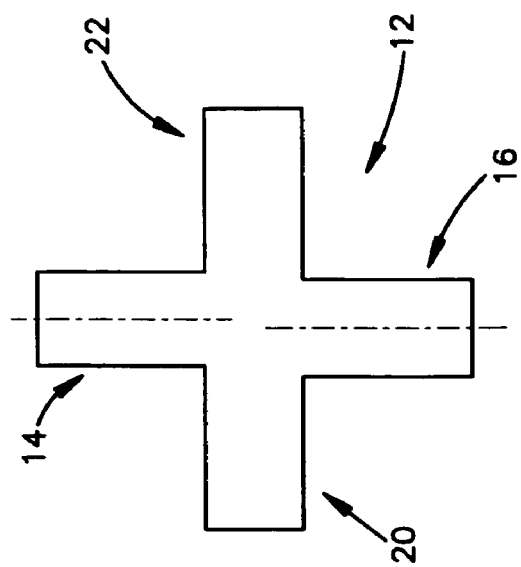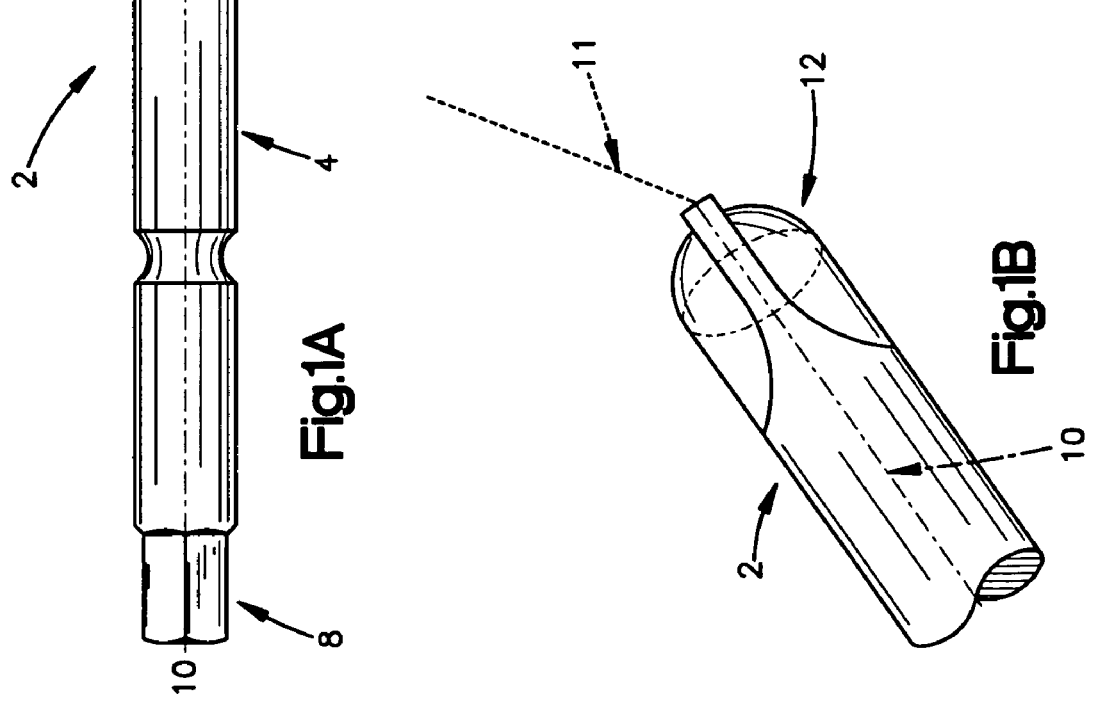

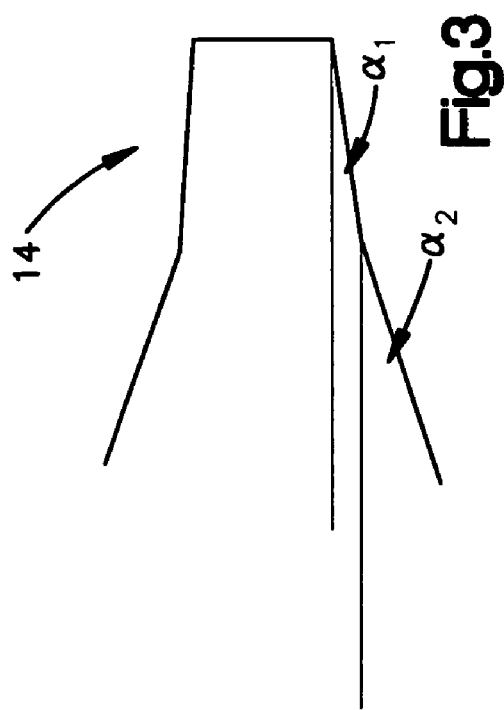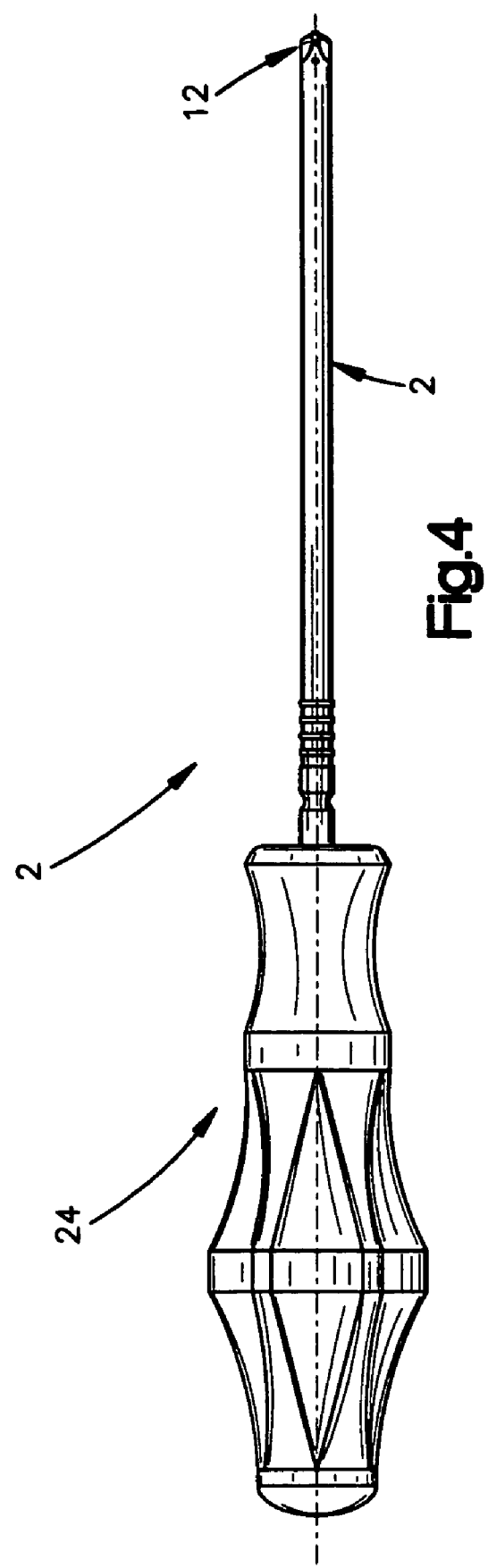

US 7,690,282 B2

SCREW-RETAINING SCREWDRIVER

CROSS-REFERENCE TO RELATION APPLICATION

This application is a continuation of U.S. Provisional Application No. 60/705,668, filed Aug. 3, 2005, the entirety of which is incorporated by reference herein.

FIELD OF THE INVENTION

The invention relates to a screwdriver having a retention mechanism for temporarily holding a screw in place on it tip while the screw is being positioned, rotated or removed. More particularly, the invention relates to a screwdriver with a cruciform head used in the installation and removal of bone screws during maxillofacial surgery.

BACKGROUND OF THE INVENTION

A variety of medical procedures, such as maxillofacial surgery, require the use of screws that are driven into a patient's bone and may at a later time be removed. Prior to being driven into the bone the screw must be maneuvered into place and following removal of the screw it is necessary to maneuver the screw out of the body without dropping the screw. A dropped screw may become lost inside the patient or may become located in a position from which it is difficult to remove.

Further in both installation of screws into bone and removal of screws from the bone it may be necessary to apply considerable torque to the screw. Thus, a secure coupling between the screwdriver tip and the screw is necessary to allow the transmission of such torque and to prevent undesirable lateral movement that may cause misalignment of the screw.

Finally there may be only restricted access to the patient site so use of a second apparatus to position or secure the screw may be impractical, such as when used through a cannula.

Thus, it is desirable to have a single apparatus that has a tip capable of securely and temporarily engaging and retaining the screw. Additionally, it is sometimes necessary to drive a screw with the axis of the blade at an angle to the axis of the screw, such as in difficult or minimally-invasive approaches.

SUMMARY OF THE INVENTION

The object of the invention is to provide a screwdriver with a retaining mechanism upon its tip for retaining a screw. The objective is accomplished with by a screwdriver comprising a shaft with a proximal end and a distal end; a tip connected to the proximal end of the shaft and consisting at least a first blade and a second blade, where the plane of the first blade and the plane of the second blade are perpendicular to the longitudinal axis of the shaft, on opposing sides of the longitudinal axis and are parallel to each other and offset in a direction perpendicular to their plane. This offset causes a friction force between the blades and a screw slot when the blade is inserted into the screw slot with force, causing the blade to retain the screw. This is known as an interference fit.

In another embodiment of the invention the screwdriver contains a third blade and a fourth blade connected to the proximal end of the shaft and which are substantially coplanar, perpendicular to the first and second blade, located along the longitudinal axis and substantially forming a cruciform enabling the apparatus to be used with screws with cruciform type slots in their head.

In a further embodiment the screwdriver contains a nub extending beyond the proximal end of the tip along the longitudinal axis of the apparatus. The nub engages a corresponding recess in a screw head assisting in guiding the blade into place in operation.

In yet another embodiment the screwdriver contains a handle operatively connected to the distal end of the shaft allowing a convenient way of applying torque to the shaft using human or other external power, such as battery power.

In yet another embodiment the screwdriver contains blades that are tapered along the longitudinal axis with the taper having its narrowest point at the proximal end of the apparatus. The taper assists in creating a secure fit between the blade and the screw slot when the The offset between the first blade and the second blade may be between 0.2 and 0.02 mm. The head of the tip may have a substantially cruciform cross section. The distal end of the shaft may be connected to a coupling section. The device may be used to drive screws with a major diameter from about 0.5 mm to about 10 mm.

BRIEF DESCRIPTION OF THE DRAWINGS

Preferred features of the present invention are disclosed in the accompanying drawings, wherein similar reference characters denote similar elements throughout the several views, and wherein:

FIG. 1A is a plan view of a preferred embodiment of the screwdriver;

FIG. 1B is an enlarged partial perspective view of the screwdriver of FIG. 1A, showing in more detail the spherically cut tip;

FIG. 2A is a cross-section of the screwdriver tip along the line A-A of FIG. 1, showing a flathead design and offset tines;

FIG. 2B is a cross-section of an alternative screwdriver tip along the line A-A of FIG. 1, showing a cruciform design and offset tines;

FIG. 3 is a cross-section of the screwdriver tip along the line B-B of FIG. 1, showing the taper of the tines; and FIG. 4 is a plan view of a second preferred embodiment of the screwdriver showing a handle.

DETAILED DESCRIPTION OF THE INVENTION

FIG. 1A shows a screwdriver 2 suitable for the present invention. The screwdriver 2 may include an elongated member 4 with a proximal end 6, a distal end 8 and which defines the longitudinal axis 10 of the screwdriver. A tip 12 may extend from the proximal end 6 of the elongated member 4 along the longitudinal axis 10.

FIG. 1B shows the tip 12 of the screwdriver 2 of FIG. 1A in more detail. Specifically, the spherically cut tip 12 may allow the blades of the screwdriver 2 to pivot in the recess of a screw so that the screw may be driven in an axis 11 not aligned with the longitudinal axis 10 of the screwdriver 2. This may be beneficial in minimally invasive or otherwise difficult procedures.

As seen in more detail in FIG. 2A, the tip 12 may have at least a first blade 14 and a second blade 16 each with a surface perpendicular to the longitudinal axis 10 of the elongated member 4. The first and second blade 14, 16 may be substantially opposite about the longitudinal axis 10, but may be offset from one another in the direction perpendicular to their surface. The offset design may cause the outer surfaces of the first and second blade 14, 16 to press against the walls of a screw slot as they are inserted into the slot creating friction along the slot wall and may cause the screw to be retained on the screwdriver tip 12. This is believed to be beneficial to creating an effective frictional fit, as previous designs have only featured a frictional relationship along the edges of the screw head. This tip 12 design is preferably used in conjunction with a flat head type screw, though other designs are contemplated.

A nub 18 may extend from the distal end of the tip along the longitudinal axis 10 of the screwdriver. The nub 18 may be sized to engage a corresponding cavity in the center of the screw head and may allow the screwdriver to be more easily positioned and more easily engage the screw.

In a preferred embodiment of FIG. 2B, the blade may have a third blade 20 and a fourth blade 22 that each have a surface perpendicular to the longitudinal axis 10 and each substantially opposite the other about the longitudinal axis 10. The third blade 20 and fourth blade 22 may be perpendicular to the first blade 14 and the second blade 16 producing a cruciform type screwdriver blade suitable for use with screws with a cruciform head slot. The third blade 20 and fourth blade 22 may be offset from one another in a direction perpendicular to their surface.

The proximal end of each blade may be tapered in the direction of the longitudinal axis. A taper allows the effective thickness of the blade to increase as it is inserted into the screw slot ensuring a better fit between the screw slot and the blade. The taper may be substantially linear with a constant gradient. Alternatively as shown in FIG. 3, the taper may occur in stages with a more acute taper of angle $\alpha_1$ on the proximal end of the blade followed by a wider taper of angle $\alpha_2$. Such a two stage taper may be advantageous as the more proximal acute taper may aid in aligning the screwdriver with the slots of screw and the wider taper following may aid in creating a better fit between the screwdriver blade and the screw as the blade is pushed deeper into the screw slot.

The elongated member 4 and tip 12 may be made of a material or combination of materials that is biocompatible, and that has the physical strength to resist the turning forces it is subject to in use and is resilient to the heat and chemical strains placed on the material in typical sterilization procedures. Such materials may include stainless steel, titanium, and titanium alloys.

The screwdriver 2 may be used with a number of types of screws including but not limited to self-drilling screws, self-tapping screws and locking screws Generally the screw will have at least one slot with a depth and width. The screw may also have a recess located at the center of the screw head for engaging the nub 18 of the screwdriver 2.

One of skill in the art will appreciate that the exact design and dimensions of the tip 12 will vary depending on the dimensions and tolerances of the chosen screws for which use is envisaged. Generally screws with larger slots will dictate a screwdriver tip 12 having blades with larger thickness and larger offsets. And screws machined with higher slot width tolerances and with shallower slots may require a tip 12 with a lesser thickness, lesser offsets and greater wedge gradients.

An exemplary screwdriver 2 for use in conjunction a screw of with a head having a diameter between about 1.5 mm and about 2 mm, a slot of about 0.6 mm width machined to a tolerance of about +/−0.05 mm, and with a depth of about 0.75 mm; may be used in conjunction with a tip 12 having blades having a thickness of about 0.5 mm and an offset of about 0.08 mm machined to a tolerance of about +/−0.01 mm with an edge taper of an angle of about 0.76 degrees for the first about 0.3 mm, and an angle of about 3.72 degrees thereafter.

Another exemplary screwdriver 2 for use in conjunction a screw of with a head of about 1.3 mm diameter, a slot of about 0.42 mm width machined to a tolerance of about +/−0.02 mm, and with a depth of 0.65 mm; may be used in conjunction with a tip 12 with blades having a thickness of about 0.4 mm and an offset of about 0.7 mm machined to a tolerance about +/−0.01 mm, with an edge taper of with an angle of about 1.90 degrees for the first about 0.3 mm and an angle of about 8.53 degrees thereafter.

These dimensions are exemplary, as variations of one or all of such dimensions are contemplated, and will be appreciated by those of skill in the art. Moreover, the tolerances given are also exemplary, as it may be preferable to have greater or lesser tolerances.

In a second preferred embodiment shown in FIG. 4 the apparatus may contain a handle 24 operatively connected to the distal end. The handle 24 that may be made from a variety of materials, most preferably those materials that are biocompatible and resilient to the heat and chemical treatments commonly used in sterilization processes. One such suitable material is silicone. The handle 24 may be contoured such that it is comfortably and securely held by the human hand.

In an alternative embodiment, the apparatus may be attached to a power driver or other rotation mechanism for rotating the apparatus. In a further alternative embodiment, the distal end of the elongated member may be attached to a coupling member such that the screwdriver may be interchangeably connected to a variety of devices that are capable of rotating the apparatus. The coupling member may take many forms including being of principally octagonal cross section or principally rectangular cross section although one of skill in the art will realize that many other designs are possible.

The description contained herein is for purposes of illustration and not for purposes of limitation. Changes and modifications may be made to the embodiments of the description and still be within the scope of the invention. Furthermore, obvious changes, modifications or variations will occur to those skilled in the art.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art which will embody the principles of the invention and fall within the spirit and the scope thereof.

What is claimed:

1. A tool for rotating and retaining a screw comprising:
a shaft having a longitudinal axis, a proximal end, and a distal end;
a tip connected to the proximal end of the shaft having at least a first blade and a second blade, wherein each blade defines a plane, the plane of the first blade and the plane of the second blade are perpendicular to the longitudinal axis of the shaft, on opposing sides of the longitudinal axis, and are parallel to each other and offset with respect to the longitudinal axis in a direction perpendicular to their plane for collectively engaging a non-offset portion of the screw to create an interference fit between the tip and the screw, wherein (i) at least one blade has a two stage taper, and (ii) the narrowest point of the taper is at the proximal end of the tool allowing the effective thickness of the blade to increase as it is inserted into the screw to thereby create a better fit between the screw and the blade.

2. The tool of claim 1, wherein the tool further comprises a third blade and a fourth blade connected to the proximal end of the shaft, and which are substantially coplanar, and perpendicular to the first and second blade to substantially form a cruciform.

3. The tool of claim 1, wherein the tool further comprises a nub extending beyond the proximal end of the tip along the longitudinal axis of the tool.

4. The tool of claim 1, wherein the tool further comprises a handle operatively connected to the distal end of the shaft.

5. The tool of claim 1, wherein the head of the tip has a substantially cruciform cross-section.

6. The tool of claim 1, wherein the distal end of the shaft is connected to a coupling section.

7. The tool of claim 1, wherein at least a portion of the tip has a spherical radius.

8. The tool of claim 1, wherein the offset between the first blade and second blade is between 0.2 mm and 0.02 mm.

9. The tool of claim 1, wherein the two-stage taper comprises a first taper that causes the at least one blade to increase in thickness at a first rate in a direction from the proximal end toward the distal end, and a second taper that causes the at least one blade to increase in thickness at a second rate in a direction from the proximal end toward the distal end, and the second rate is different than the first rate.

10. The tool of claim 9, wherein the second taper is disposed distal of the first taper, and the second rate is greater than the first rate.

11. The tool of claim 9, wherein the first taper defines a first acute angle with respect to the longitudinal axis, the second taper defines a second acute angle with respect to the longitudinal axis, and the first and second angles are different.

12. The tool of claim 11, wherein the second angle is greater than the first angle.

13. The tool of claim 12, wherein the second taper is disposed distal of the first stage taper.

14. The tool of claim 13, wherein the second stage taper is connected to the first stage taper.

15. A tool for rotating and retaining a screw comprising:
a shaft having a longitudinal axis, a proximal end, and a distal end;
a tip connected to the proximal end of the shaft having at least a first blade and a second blade that are fixed from movement relative to each other, and define respective planes, wherein the plane of the first blade and the plane of the second blade are perpendicular to the longitudinal axis of the shaft, on opposing sides of the longitudinal axis, and are parallel to each other and offset in a direction perpendicular to their plane for collectively engaging a non-offset portion of the screw to create an interference fit between the tip and the screw, wherein at least a portion of the tip has a spherical radius.

16. The tool of claim 15, wherein the tool further comprises a third blade and a fourth blade connected to the proximal end of the shaft, and which are substantially coplanar, and perpendicular to the first and second blade to substantially form a cruciform.

17. The tool of claim 15, wherein the tool further comprises a nub extending beyond the proximal end of the tip along the longitudinal axis of the tool.

18. The tool of claim 15, wherein the tool further comprises a handle operatively connected to the distal end of the shaft.

19. The tool of claim 15, wherein at least one blade has a taper, and wherein the narrowest point of the taper is at the proximal end of the tool.

20. The tool of claim 15, wherein the head of the tip has a substantially cruciform cross-section.

21. The tool of claim 15, wherein the distal end of the shaft is connected to a coupling section.

22. The tool of claim 15, wherein at least one of the blades has a first taper that defines a first acute angle with respect to the longitudinal axis, and a second taper that defines a second acute angle with respect to the longitudinal axis, and the first and second angles are different.

23. The tool of claim 22, wherein the second angle is greater than the first angle.

24. The surgical tool of claim 23, wherein the second taper is disposed distal of the first stage taper.

25. The tool of claim 24, wherein the second stage taper is connected to the first stage taper.

26. A surgical tool for rotating and retaining a screw in a bone, the surgical tool comprising:
a surgical shaft having a longitudinal axis, a proximal end, and a distal end;
a surgical tip connected to the proximal end of the shaft having a first blade and a second blade and no other blades, wherein each blade defines a plane, the plane of the first blade and the plane of the second blade are perpendicular to the longitudinal axis of the shaft, on opposing sides of the longitudinal axis, are parallel to each other and offset in a direction perpendicular to their plane for collectively engaging a non-offset portion of the screw to create an interference fit between the tip and the screw, each of the first and second blade defines opposing edges that extend parallel to their respective plane, no portion of the first blade extends perpendicular with respect to the plane of the first blade, and no portion of the second blade extends in a direction perpendicular to the plane of the second blade.

27. The surgical tool of claim 26, wherein at least a portion of the tip has a spherical radius.

28. The surgical tool of claim 26, wherein the tip is a flat-head tip.

29. The surgical tool of claim 26, wherein at least one of the blades has a first taper that defines a first acute angle with respect to the longitudinal axis, and a second taper that defines a second acute angle with respect to the longitudinal axis, such that the first and second angles are different.

30. The surgical tool of claim 29, wherein the second angle is greater than the first angle.

31. The surgical tool of claim 30, wherein the second stage taper is disposed distal of the first stage taper.

32. The surgical tool of claim 31, wherein the second stage taper is connected to the first stage taper.

33. The surgical tool of claim 26, wherein at least one of the blades has a thickness that increases at a first rate and a second different rate in a direction from the proximal end towards the distal end.

34. The surgical tool of claim 33, wherein the second rate is higher than the first rate, and the thickness increases at the second rate at a location distal of a location where the thickness increases at the first rate.

* * * * *